United States Patent [19]

Linstid, III

[11] Patent Number: 4,579,967

[45] Date of Patent: Apr. 1, 1986

[54] PRODUCTION OF ALKYL METHACRYLATE

[75] Inventor: H. Clay Linstid, III, Maplewood, N.J.

[73] Assignee: Celanese Corporation, New York, N.Y.

[21] Appl. No.: 464,270

[22] Filed: Feb. 7, 1983

[51] Int. Cl.[4] .................. C07C 67/30; C07C 69/675; C07D 301/19

[52] U.S. Cl. .................................. 560/212; 560/129; 560/179; 560/214; 549/529

[58] Field of Search ............... 568/571, 574, 575, 569; 560/179, 212, 214, 129; 549/529; 502/350

[56] References Cited

U.S. PATENT DOCUMENTS

| | | | |
|---|---|---|---|
| 3,022,336 | 2/1962 | Sennewald et al. | 560/212 |
| 3,068,275 | 12/1962 | Fuchs | 560/179 |
| 3,974,207 | 8/1976 | Szelejewski et al. | 560/179 |
| 3,983,143 | 9/1976 | Sheng et al. | 549/529 |
| 4,201,875 | 5/1980 | Wu et al. | 568/575 |

OTHER PUBLICATIONS

Kaloustian et al., *Bull. Soc. Chim. Fr.* pp. 4411–4417, (1971).

*Primary Examiner*—Natalie Trousof
*Assistant Examiner*—Bruce D. Gray
*Attorney, Agent, or Firm*—Depaoli & O'Brien

[57] ABSTRACT

This invention provides a process for converting alkyl isobutyrate to alkyl methacrylate via alkyl-hydroperoxy-isobutyrate and alkyl alpha-hydroxyisobutyrate intermediate.

An important aspect of the process is the use of a particulate metal oxide substrate in the first step of the process.

1 Claim, No Drawings

PRODUCTION OF ALKYL METHACRYLATE

BACKGROUND OF THE INVENTION

Alkyl methacrylates are an important class of chemical commodities which are produced worldwide on a commercial scale. Economic considerations indicate that the routes to methyl methacrylate derived from propylene have an economic advantage over synthesis methods based on isobutylene or ethylene. Methyl methacrylate currently is derived primarily from propylene via cumene formation and conversion to acetone and phenol. The acetone is then subjected to cyanation, hydrolysis and esterification steps.

A prospective alternative propylene based synthesis of methyl methacrylate proceeds via an intermediate isobutyric acid or methyl isobutyrate obtained by carbonylation of propylene. A variety of acid catalyzed (e.g., Koch reaction) and metal catalyzed carbonylation of propylene reactions are known to proceed in good yield. Oxidative dehydrogenation of isobutyric acid to methacrylic acid can be accomplished in a relatively good yield employing a heteropoly acid catalyst. However, there is no effective means for converting methyl isobutyrate directly to methyl methacrylate. In general, oxidative dehydrogenation conditions are too severe and cause hydrolysis and decarboxylation.

One method proposed for the conversion of methyl isobutyrate is by oxidation of methyl isobutyrate to the corresponding α-hydroperoxide followed by reduction of the α-hydroperoxide with propylene to provide methyl α-hydroxyisobutyrate and propylene oxide, and then a subsequent dehydration of the methyl α-hydroxyisobutyrate to yield the desired methyl methacrylate:

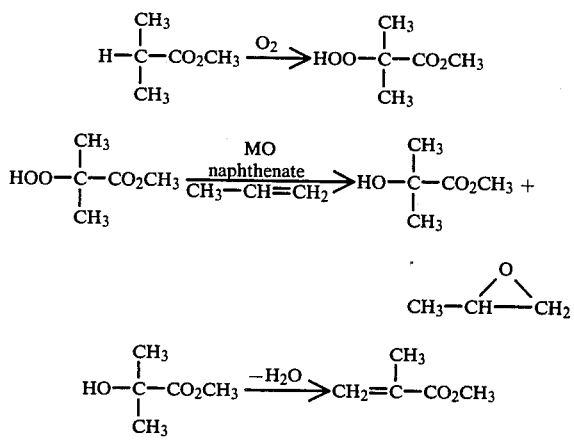

Results reported in Bull. Soc Chim. Fr., 411–4417 (1971) indicate that t-butyl α-hydroperoxyisobutyrate can produce propylene oxide from propylene in 84% yield with a molybdenum naphthenate catalyst. In addition, the dehydration of methyl α-hydroxyisobutyrate is described in U.S. Pat. No. 3,974,207.

One disadvantage of the above prospective reaction scheme for converting methyl isobutyrate to methyl methacrylate is the low reaction rate and yield obtained in the first step oxidation of methyl isobutyrate to methyl α-hydroperoxyisobutyrate. The French publication recited above reports a best yield of 13% after a 68 hour oxidation period.

Accordingly, it is an object of this invention to provide a process for converting alkyl isobutyrate to alkyl methacrylate.

It is another object of this invention to provide a process for producing methyl methacrylate and propylene oxide.

It is a further object of this invention to provide a process for converting alkyl isobutyrate to the corresponding α-hydroperoxyisobutyrate with an improved combination of conversion rate and selectivity.

Other objects and advantages of the present invention shall become apparent from the accompanying description and example.

DESCRIPTION OF THE INVENTION

One or more objects of the present invention are accomplished by the provision of a process for production of alkyl methacrylate which comprises (1) reacting alkyl isobutyrate with molecular oxygen in a liquid phase medium in the presence of a particulate solid substrate selected from oxidic compounds of magnesium, calcium, titanium, zirconium, vanadium, zinc, aluminum and barium metals, to form alkyl α-hydroperoxyisobutyrate; (2) contacting the alkyl α-hydroperoxyisobutyrate with alkene in a liquid phase medium to form α-hydroxyisobutyrate and alkylene oxide as coproducts; (3) recovering the alkyl α-hydroxyisobutyrate and dehydrating it in a liquid phase medium under acidic conditions to form alkyl methacrylate product.

The term "alkyl" as employed herein is meant to include $C_1$–$C_8$ alkyl substituents such as methyl, ethyl, propyl, butyl, isobutyl, tertiary-butyl, hexyl, octyl, and the like.

The term "alkene" as employed herein is meant to include $C_2$–$C_{10}$ alkylene compounds such as propylene, butylene, isobutylene, hexylene, octylene, decylene, and the like, wherein the olefinic unsaturation can be either in a terminal or non-terminal position. The alkene compounds can contain heteroatoms such as nitrogen, oxygen, sulfur or halogen which do not interfere with the efficiency of the step (2) oxidation reaction.

The term "alkylene oxide" as employed herein refers to the epoxidation derivative of the alkene reactant in step (2) of the process.

Alkyl Isobutyrate Oxidation

The reaction can be conducted conveniently in a closed reactor system, preferably with glass or ceramic surfaces in contact with the liquid reaction medium.

The reactor is charged with alkyl isobutyrate and particulate solid substrate, and pressured with molecular oxygen or a molecular oxygen-containing gas medium. In a typical procedure the reactor is pressured with oxygen-enriched air to a pressure between about 50–150 psi. Increasing the partial pressure of molecular oxygen up to about 100 psi tends to enhance the yield of alkyl α-hydroperoxyisobutyrate.

Optionally, an inert solvent such as perfluorinated hydrocarbons may be employed, as well as a free radical initiator such as di-tertiary-alkyl peroxides, e.g., di-tertiary-butyl peroxide. A slight increase in oxidation efficiency is observed with di-tertiary-butyl peroxide as an initiator.

The step (1) oxidation reaction is conducted at a temperature between about 50°–200° C., and preferably at a temperature between about 120°–160° C. At a temperature below about 120° C. the reaction proceeds at a slow rate. At a temperature above about 160° C. the reaction is rapid, but there is loss of alkyl 60-hydroperoxyisobutyrate due to thermal decomposition.

An essential aspect of the step (1) oxidation system is the presence of a particulate solid substrate selected from oxidic compounds of magnesium, calcium, titanium, zirconium, vanadium, zinc, aluminum and barium metals. The presence of magnesium oxide or titanium oxide in the step (1) oxidation reaction medium provides the optimal selectivity of alkyl isobutyrate to the corresponding alkyl α-hydroperoxyisobutyrate product.

The particulate metal oxide is employed in a quantity between about 0.1–10 weight percent, and preferably between about 0.5–5 weight percent, based on the weight of alkyl isobutyrate reactant.

The beneficial effect of the particulate metal oxide appears to be at least partially related to the surface area of the metal oxide power. The Tyler mesh size of the finely divided metal oxide preferably is less than about 100 mesh, and most preferably less than about 300 mesh. The presence of strongly basic or strongly acidic impurities in the metal oxide substrate tends to lower the overall efficiency of the oxidation reaction, due in part to secondary reactions involving the alkyl α-hydroperoxyisobutyrate product.

The alkyl α-hydroperoxyisoburyrate product can be recovered in pure form by distillation of the oxidation reaction medium after the oxidation phase is completed. Alternatively, the oxidation reaction medium containing the alkyl α-hydroperoxyisobutyrate can be employed directly in step (2) of the process, with or without the removal of the metal oxide solid phase.

Formation Of Alkyl α-hydroxyisobutyrate

In step (2) of the process, alkyl α-hydroperoxyisobutyrate is admixed with an alkene coreactant in a liquid phase medium to form alkyl α-hydroxyisobutyrate and alkylene oxide as coproducts. The proportions of the coreactants can be varied over a wide range, but generally the alkyl α-hydroxyisobutyrate is charged to a reactor and, in the case of a gaseous alkene such as propylene, the reactor is pressured with alkene in a large molar excess relative to the hydroperoxide coreactant, e.g., a tenfold excess.

In effect, step (2) of the process represents an epoxidation of an alkene compound with an epoxidation reagent, i.e., the alkyl α-hydroperoxyisobutyrate coreactant.

It is desirable to employ a catalyst for the step (2) epoxidation reaction. Particularly advantageous is the use of a molybdenum or vanadium compound. A preferred catalyst is a molybdenum compound such as molybdenum naphthenate, molybdenum acetylacetonate, polymolybdic acid, and the like. The catalyst is employed in a quantity between about 0.01–5 weight percent, based on the weight of alkyl α-hydroperoxyisobutyrate reactant.

The step (2) reaction is conducted at a temperature between about 20°–120° C., and a pressure between about 15–500 psi. An inert solvent may be employed as a reaction medium if desired.

The alkyl α-hydroxyisobutyrate and alkylene oxide coproducts can be recovered in pure form by conventional methods such as fractional distillation.

Production Of Alkyl Methacrylate

In step (3) of the process, in a manner similar to that in U.S. Pat. No. 3,974,207 alkyl α-hydroxyisobutyrate is dehydrated in a liquid phase medium under acidic conditions to yield alkyl methacrylate. It is preferred to include a free radical polymerization inhibitor such as hydroquinone in the reaction medium, to suppress any polymerization of the alkyl methacrylate product.

The acidic conditions can be provided by aqueous mineral acid (e.g., sulfuric acid), in which case a water-miscible solvent such as butanol can be employed if a single phase reaction medium is desired. An organic acid such as acetic acid or p-toluenesulfonic acid can be used instead of a mineral acid.

A preferred method of dehydration is by contacting the alkyl α-hydroxyisobutyrate feed with an acidic cation exchange resin, e.g., a sulfonic acid cation exchange resin in the acid form. In U.S. Pat. No. 3,974,207 methyl α-hydroxyisobutyrate is passed through a column to effect dehydration to methyl methacrylate. The dehydration can also be conducted in the vapor phase over a heterogeneous catalyst such as alumina, slica, zeolite, and the like.

The step (3) dehydration reaction when in a liquid medium is conducted at a temperature between about 50°–150° C., and preferably at a temperature between about 70°–120° C. at ambient pressure.

The alkyl methacrylate product is recovered by distillation, preferably in the presence of a plymerization inhibitor.

The following Example is further illustrative of the present invention. The specific ingredients and processing parameters are presented as being typical, and various modifications can be derived in view of the foregoing disclosure within the scope of the invention.

EXAMPLE

This example illustrates the present invention improved method of oxidizing alkyl isobutyrate to alkyl α-hydroperoxyisobutyrate, and the subsequent conversion of the α-hydroxyperoxide product to alkyl methacrylate.

A series of reaction runs are conducted in 3 oz. glass Fisher-Porter bottles equipped with a gas inlet and a pressure gauge. All stainless steel parts are treated with nitric acid to passivate the surfaces toward free radical reactions. Under reaction conditions the liquid phase contacts only glass surfaces. Stirring is accomplished with a magnetic stirring bar. The reaction bottles are placed in an oil bath heated to 140° C.

A 15 g quantity of methyl isobutyrate is charged to each reaction bottle, and additionally a solid inorganic oxide powder is charged in a quantity as indicated in the Table.

The total pressure in each bottle during the reaction is about 55 psi, with the partial pressure of oxygen being about 43 psi. The oxidation is conducted for a two hour reaction period.

The yield of methyl α-hydroxyperoxyisobutyrate is determined by iodimetric titration, in a manner similar to that described in Anal. Chem., 36, 195 (1964). Gas chromatographic analysis are performed with a Varian 3700, employing Porapak Q in 10 ft. of 1/8" o.d. nickel tubing (180° C., He at 30 ml/min).

The comparative data in the Table demonstrate that the presence of a specific type of metal oxide compound in the form of a finely divided solid substrate improves the selectivity and overall efficiency of the oxidation of methyl isobutyrate to the corresponding α-hydroperoxide product. The runs conducted with silver metal or silver oxide result in a lower efficiency to α- hydroperoxide product than when no solid inorganic powder component is employed in the oxidation reaction.

The methyl α-hydroperoxyisobutyrate product is employed to oxidize propylene to propylene oxide (in a yield of at least 80%) in the presence of a molybdenum naphthenate catalyst, with the concurrent production of α-hydroxyisobutyrate, in a manner similar to that described in Bull. Soc. Chim. Fr., 4415 (1971).

Methyl α-hydroxyisobutyrate is dehydrated to methyl methacrylate in at least about 70% yield by passage of the ester (and 0.1% hydroquinone) through a column of sulfonic acid cation exchange resins at 100° C., in a manner similar to that illustrated in U.S. Pat. No. 3,974,207.

TABLE

| Run | Solid Additive | Wt % Added | Yield, Mole % | | | | % Conversion of MIB | % Selectivity to MHPIB |
|---|---|---|---|---|---|---|---|---|
| | | | $CH_3OH$ | $CH_3\overset{O}{\overset{\|}{C}}CH_3$ | MHIB | MHPIB | | |
| 1 | — | — | 3.12 | 4.77 | 1.37 | 0.728 | 6.14 | 11.9 |
| 2 | MgO | 1.01 | 1.53 | 2.05 | 1.35 | 2.00 | 3.40 | 58.8 |
| 3 | CaO | 1.01 | 3.61 | 4.60 | 2.06 | 0.949 | 6.66 | 14.2 |
| 4 | ZnO | 1.00 | 1.21 | 2.12 | 1.45 | 1.67 | 3.57 | 46.8 |
| 5 | ZnO | 1.05 | 3.20 | 3.86 | 1.77 | 0.941 | 5.63 | 16.7 |
| 6 | $Al_2O_3$ | 1.02 | 2.20 | 3.86 | 1.50 | 2.10 | 4.63 | 45.4 |
| 7 | $ZrO_2$ | 1.00 | 2.05 | 2.91 | 1.55 | 1.83 | 4.46 | 41.0 |
| 8 | BaO | 1.01 | 2.35 | 4.29 | 1.74 | 1.11 | 6.03 | 18.4 |
| 9 | $TiO_2$ | 1.01 | 2.30 | 2.60 | 1.51 | 2.08 | 4.11 | 50.6 |
| 10 | Ag | 0.14 | 2.57 | 3.83 | 1.52 | 0.153 | 5.35 | 2.7 |
| 11 | $AgO_2$ | 0.10 | 2.31 | 3.47 | 1.67 | 0.181 | 5.14 | 3.5 |

MHIB: methyl α-hydroxyisobutyrate
MHPIB: methyl α-hydroperoxyisobutyrate
MIB: methyl isobutyrate

What is claimed is:

1. A process for production of alkyl methacrylate which comprises (1) reacting alkyl isobutyrate with molecular oxygen in a liquid phase medium in the presence of a particulate solid substrate consisting essentialy of titanium oxide to form alkyl alpha-hydroperoxyisobutyrate, wherein the titanium oxide has a particle size less than about 100 mesh, and is present in a quantity between about 0.1–10 weight percent, based on the weight of alkyl isobutyrate; (2) contacting the alkyl alpha-hydroperoxyisobutyrate with alkene in a liquid phase medium to form alkyl alpha-hydroxyisobutyrate and alkylene oxide as coproducts; (3) recovering the alkyl alpha-hydroxyisobutyrate and dehydrating it in a liquid phase medium under acidic conditions to form alkyl methacrylate product.

* * * * *